United States Patent [19]

Martin et al.

[11] 4,429,008

[45] Jan. 31, 1984

[54] THIOL REACTIVE LIPOSOMES

[75] Inventors: Frank J. Martin, San Francisco; Demetrios P. Papahadjopoulos, Lafayette; Wayne L. Hubbell, Orinda, all of Calif.

[73] Assignee: The Regents of the University of California, Berkeley, Calif.

[21] Appl. No.: 329,211

[22] Filed: Dec. 10, 1981

[51] Int. Cl.³ .......................... B01J 13/02; B32B 9/02
[52] U.S. Cl. .................................. 428/402.2; 424/1.1; 424/38; 424/85; 424/88; 436/501; 436/532; 436/829
[58] Field of Search ...................... 252/316; 424/1, 36, 424/1.1, 38; 436/829, 501; 428/402.2

[56] References Cited

U.S. PATENT DOCUMENTS

| 3,516,941 | 6/1970 | Matson ............................ 264/4.7 X |
| 3,850,578 | 11/1974 | McConnell . |
| 3,887,698 | 6/1975 | McConnell et al. . |
| 4,193,983 | 5/1978 | Ullman et al. . |
| 4,199,565 | 4/1980 | Fullerton ............................. 424/89 |
| 4,342,739 | 8/1982 | Kakimi et al. .................. 252/316 X |

OTHER PUBLICATIONS

Martin, F., "Immunospecific targeting of Liposomes to Cells: A Novel and Efficient Method . . . Disulfide Bonds", Biochemistry 20, (Jul. 1981) 4229-4238.
Torchilin, V. P., et al., "Incorporation of Hydrophilic Protein . . . into Liposome Membrane", Biochimica et Biophysica Acta, 602 (1980) 511-521.
Torchilin, V. P., et al., "Preservation of Antimyosin . . . to Liposomes", Biochemical and Biophysical Research Communications, 89, #4, (1979) 1114-1119.
Huang, A. et al., "Monoclonal Antibody Covalently and coupled with Fatty Acid", Journal of Biological Chemistry255, #17, (1980) 8015-8018.
Torchilin, V. P., et al., "Coating Liposomes with Protein Decreases their Capture by Macrophages", FEBS Letters, 111 #1, (1980) 184-188.
Leserman, L. et al., "Targeting to Cell of Fluorescent Liposomes . . . or Protein A.", Nature 228 (Dec. 11, 1980) 602-604.
Heath, T. et al., "Antibody Targeting of Lipsomes: Cell . . . to Vesicle Surface," Science 210 (Oct. 31, 1980) 539-541.
Heath, T. et al., "Covalent Attachment of Immunoglobulins to Liposomes via Glycosphingolipids," Biochimica et Biophysica Acta, 640 (1981) 66-81.
Torchilin, V.P. et al., "Comparative Studies on Covalent . . . on the Surface of Liposomes", BBRC, vol. 85, No. 3, pp. 983-990 (1978).
Sinha, D. et al., "Conjugation of a Hydrophobic Anchor . . . to Liposomal Membranes", FEBS Proc. Abstracts, (May 1, 1980).
Sinha, D. et al., "Attachment to Membranes of Exogenous . . . to a Hydrophobic Anchor", BBRC, vol. 90, No. 2, (1979), 554-560.
Carlsson, J. et al., "Protein Thiolation and Reversible Protein-Protein Conjugation", Biochem. J., 173, (1978) 723-737.
Oeltmann, et al., "A Hybrid Protein Containing the Toxic . . . of Human Chorionic Gonadotropin", J. Bio. Chem., vol. 254, No. 4, (1979), 1022-1027.
Rector, et al., "A Method for the Preparation . . . of Predetermined Composition", J. Immuno. Methods, 24, (1978) 321-326.
Leserman, L. D., et al., "Specific Cellular Targeting and Drug Transfer from Liposomes Bearing Monoclonal Antibodies", Nature, vol. 293, pp. 226 (1981).
Barbet, et al., "Monoclonal Antibody Covalently Coupled to Liposomes", J. Supramolec. Structure and Cellular Biochem., vol. 16, pp. 243-258 (1981).

Primary Examiner—Richard D. Lovering
Attorney, Agent, or Firm—Majestic, Gallagher, Parsons & Siebert

[57] ABSTRACT

Liposomes are provided which have a plurality of thiol reactive groups extending outward of the liposomal bilayer. The liposomes form stable covalent bonds with ligands having thiol groups, such as Fab' fragments. Particularly preferred liposomes include maleimide moieties as the thiol reactive groups. The thiol reactive liposomes are usefully employed in agglutination assays, such as blood typing and binding inhibitions, and targeting to specific cells.

10 Claims, No Drawings

THIOL REACTIVE LIPOSOMES

FIELD OF THE INVENTION

The present invention relates generally to liposomes, and more particularly to liposomes which may encapsulate materials, such as drugs, nucleic acids, proteins, reporter molecules and the like, and which have a plurality of thiol reactive groups connected to and extending from the lipid bilayer. These thiol reactive liposomes may be readily and efficiently covalently bound to a variety of ligands having thiol groups for uses such as the specific targeting of chemotherapeutic agents, as immunodiagnostic agents, and the like.

The invention described herein was made in the course of work under a grant or award from the Department of Health and Human Services.

BACKGROUND OF THE INVENTION

Liposomes are unilamellar or multilamellar lipid vesicles which enclose a three-dimensional space. The lipid membranes of liposomes are formed by a bimolecular layer of one or more lipid components having polar heads and non-polar tails. In an aqueous solution, the polar heads of one layer orient outwardly to extend into the aqueous solution and to form a continuous, outer surface. Unilamellar liposomes have one such bimolecular layer, whereas multilamellar vesicles generally have a plurality of substantially concentric bimolecular layers arranged rather like an onion.

Liposomes are well recognized as useful for encapsulating therapeutic agents, such as cytotoxic drugs or other macromolecules capable of modifying cell behavior, and carrying these agents to in vivo sites. For example, U.S. Pat. No. 3,993,754, inventors Rahman et al., issued Nov. 23, 1976, discloses an improved method for chemotherapy of malignant tumors in which an antitumor drug is encapsulated within liposomes and the liposomes are injected into an animal or man. U.S. Pat. No. 4,263,428, inventors Apple, et al., issued Apr. 21, 1981, discloses an antitumor drug which may be more effectively delivered to selective cell sites in a mammalian organism by incorporating the drug within uniformly sized liposomes. Thus, drug administration via liposomes can have reduced toxicity, altered tissue distribution, increased drug effectiveness, and an improved therapeutic index. Liposomes have also been used in vitro as valuable tools to introduce various chemicals, biochemicals, genetic material and the like into viable cells.

However, a deficiency of liposomal drug delivery has been the inability to quantitatively or selectively direct the liposomes' contents to specific sites of action over a therapeutically meaning time frame.

It has been suggested that target, or site, specificity might be conferred on liposomes by their association with specific antibodies or lectins. Methods of associating antibodies with liposomes have been described and may be generally divided into two groups—nonspecific association and covalent attachment.

Non-specific association appears to rely upon the affinity of the Fc portion of the antibody for the hydrophobic region of the lipid bilayer. This has little practical value because the liposomes are rendered more permeable to their encapsulated contents and may themselves be aggregated. Further, it is not believed that this complex would be sufficiently stable in plasma for the considerable periods of time believed necessary in many potential clinical applications.

Considerable effort has ensued in attempts to covalently attach protein to liposomes, with several promising results. For example, Heath et al., have reported efficiently covalently binding liposomes to biologically active proteins by periodate oxidation of glycosphingolipids. *Science,* Vol. 210, pp. 539–541 (1980). This method of liposome-antibody conjugation has bound up to about 200 μg of protein per μmole of total lipid.

SUMMARY OF THE INVENTION

It is an object of the present invention that liposomes be provided which may be readily and efficiently covalently bound to a variety of ligands bearing thiol groups to achieve reproducible, high coupling ratios without vesicle aggregation.

It is a further object of the present invention that the liposomes, following coupling with ligands, result in a highly stable ligand-vesicle linkage, and particularly result in a linkage which is stable in serum or in the presence of reducing agents.

It is a further object of the present invention that ligands, particularly antibodies, retain a substantial amount of antigen binding capacity after having been coupled to the inventive liposomes.

These and other objects of the present invention are provided by liposomes having a lipid bilayer defining an outer surface. A plurality of thiol reactive groups are integrally connected to the lipid bilayer and extend outward with respect to the outer surface. Particularly preferred embodiments of the present invention are maleimide moieties as the thiol reactive groups. A representative one of such a thiol reactive liposome is illustrated by the following structure (wherein a portion which includes a maleimide moiety is enlarged relative a diagrammatic liposome representation):

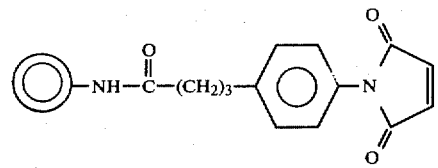

The thiol reactive liposomes may be separated from impurities by conventional techniques after formation and then stored.

Thiol reactive liposomes in accordance with the present invention form quite stable covalent bonds with ligands having thiol groups, such as Fab' fragments. For example, liposomes as above illustrated, when coupled with Fab', resulted in no coupled Fab' being lost during incubation for 24 hours in 50% human serum.

DETAILED DESCRIPTION OF THE PREFERRED EMBODIMENTS

Both naturally occurring and synthetic lipids are known and useful in forming liposomes. For example, naturally occurring lipids such as phosphoglycerides, sphingolipids, and glycolipids are all characterized by having polar head regions and non-polar tail regions which form bimolecular layers readily in aqueous systems. A variety of synthetic lipids (often differing from the naturally occurring lipids simply by having different hydrocarbon chain lengths in the non-polar tail regions) are also known and have been used to form liposomes.

In addition, components such as vitamin E (normally considered to be a lipid since it is insoluble in water but extractable with organic solvents) and the like may be included in liposomal membranes.

The fluid encapsulated by liposomes normally includes a polar liquid, or aqueous, phase into which the polar heads of the membranes' inner layer extend. The fluid may carry, either dissolved or undissolved, a wide variety of other components. For example, the fluid may include biologically active molecules, pharmaceuticals, nutrients, and reporter molecules such as radioactive ions, chemiluminescent molecules and fluorescent molecules.

Liposomes may be prepared by any of various of conventional methods known to the art. These various known methods may be generally characterized as yielding either unilamellar vesicles or multilamellar vesicles. Either liposomal structure is suitable for the present invention; however, due to the generally larger internal space available in unilamellar liposomes, the inventive liposomes are preferably prepared by the reverse-phase evaporation vesicle (REV) method, as is described in U.S. Pat. No. 4,235,871, issued Nov. 25, 1980, inventors Szoka, Jr., and Papahadjopoulos, which description is incorporated herein by reference.

Liposomes in accordance with the present invention include a plurality of thiol reactive groups. These thiol reactive groups are adapted to form either thioether bonds or disulfide bonds with ligands bearing thiol groups. The thiol reactive groups are at polar head regions of nitrogen containing lipids which are components of at least the lipid bilayer which defines an outer surface for the liposomes. (e.g. in the instance of unilamellar vesicles this lipid bilayer is the solid lipid bilayer, whereas in the instance of multilamellar vesicles, the nitrogen containing lipids are components of at least the most outward of the lipid bilayers).

A suitable nitrogen containing lipid is normally one component of two or more lipid components, or lipid mixture, constituting the liposomal membrane. When liposomes in accordance with the present invention are formed from a mixture of two or more lipid components, then the nitrogen containing lipids having thiol reactive groups bound thereto may constitute up to about 80 mole % with respect to the total lipid content.

Primary considerations in selecting the amount of nitrogen containing lipids having thiol reactive groups are that too large a concentration may lead to aggregation of the vesicles or of insufficient integrity (such as permeability) of the liposomal membrane; alternatively, too little of the nitrogen containing lipids bearing thiol reactive groups may result in inadequate coupling ratios of ligands per vesicle lipid content. For most applications, the mole % of nitrogen containing lipids having thiol reactive groups will be in an amount of about 0.01 mole % to about 80 mole %. For example, coupling ratios in excess of 250 microgram Fab' per micromole of total lipid have been reproducably obtained with about 2.5 mole %.

Any of the amphiphilic substances known to produce liposomes may be utilized. Nevertheless, some mixtures of lipids may tend to be permeable to small molecules, and cholesterol is frequently a desirable addition to some of these lipid mixtures for reducing the permeability thereof. Other components may also be utilized to reduce liposome permeability. For example, a phosphatidyl choline having the fatty acid saturated aliphatic chain, or non-polar tails, of a length of 18 (rather than the usual unsaturated 16 to 18 carbon chain obtainable from egg yolks) may be utilized.

A variety of nitrogen containing lipid precursors may be derivatized in order to bear the suitable thiol reactive groups. Thus, for example, nitrogen containing lipid precursors having primary or secondary amino groups within the polar head region may be reacted with a suitable activating group, or reagent (further discussed hereinafter), to form an amide or an amidine linkage. Suitable nitrogen containing lipid precursors include, for example, phosphatidylethanolamine, phosphatidylserine, stearylamine, glycolipids with amino substituted sugars, and the like.

The ligand is anchored to the liposome surface via a covalent bond with the nitrogen containing lipids, which are structural parts of the lipid bilayer. This may be accomplished either by derivatizing the primary or secondary amino groups of lipids in preformed liposomes, or by first derivatizing the nitrogen containing lipid precursors and then forming the inventive liposomes. The latter is preferred because of convenience in preparing the liposomes, since the derivatized lipid precursors can be prepared in advance, used to form liposomes when desired, and the resultant liposomes will automatically bear the thiol reactive groups.

As has previously been noted, thiol reactive groups of the liposomes are adapted to form disulfide or thio ether bonds with ligands bearing thiol groups. Preferred thiol reactive groups adapted to form disulfide bonds, for example with IgG fragments bearing sulfhydryl groups, are 2-Pyridyldithiol, 4-Pyridyldithiol, and thiosulphate. A particularly preferred thiol reactive group of the type adapted to form thio ether bonds, for example with IgG fragments bearing sulfhydryl groups, includes maleimide moieties.

In both instances, it is preferred that the thiol reactive groups be spaced from the amide or amidine linkages of the nitrogen containing lipids by organic spacer arms. These organic spacer arms may be composed of a wide variety of organic moieties, such as carbon chains (branched or unbranched and saturated or unsaturated) as well as rings, particularly aromatic rings such as substituted or unsubstituted phenyl moieties. Suitable organic spacer arms will not interfere with coupling reactions between the thiol reactive groups and ligands, and function to position the thiol reactive groups to extend outward of the liposomal outer surface. This positioning favors coupling reactions with ligands.

Derivatives of nitrogen containing lipids may be formed by reaction with suitable reagents. A suitable reagent may be viewed as having an amino reactive moiety at one end of the molecule, the thiol reactive group at the other end of the molecule, and the organic spacer arm therebetween.

Where the liposomes are preformed and include nitrogen containing lipid precursors, the thiol reactive groups may be incorporated via amide or amidine linkages as follows. Where the amino reactive moiety is an aldehyde, the primary or secondary amino group of a nitrogen containing lipid precursor in an aqueous solution may be reductively aminated in the presence of a reducing agent such as sodium cyanoborohydride or sodium borohydride. Where the amino reactive moiety is, for example, methyl imidate, an amidine linkage will form spontaneously in aqueous solution with a primary amino group of a nitrogen containing lipid precursor. Where the amino reactive moiety is N-succinimide, an amide linkage forms spontaneously with a primary amino group of the lipid precursor.

Where the liposomes are to be formed from a lipid mixture, the nitrogen containing lipid precursor may be derivatized as follows. A lipid solution may be formed and a suitable reagent admixed. Where the amino reactive moiety of the reagent added is an aldehyde, then the lipid may be solubilized in, for example, chloroform-:methanol (1:1). In the presence of a reducing agent, such as sodium cyanoborohydride, sodium borohydride or lithium cyanoborohydride, primary or secondary amino groups of the lipid precursor will be reductively aminated. Where the amino reactive moiety of the added reagent is methyl imidate, a primary amino group of the lipid precursor will react, in the presence of triethylamine, to form an amidine linkage. Similarly, use of a reagent having N-succinimide as the amino reactive moiety results in an amide linkage.

Once formed, the inventive liposomes having thiol reactive groups may be separated from impurities by one or a combination of techniques, such as gel chromatography, flotation in polymer gradients, and the like. The liposomes may be stored at low temperature (for example about 4° C.) as an aqueous suspension under an inert atmosphere. The liposomes may also be extruded to control their size, and may be subjected to manipulations which remove non-encapsulated materials.

Preparation of several embodiments of the present invention will now be more particularly described. Various abbreviations will sometimes be used, many of which are listed along with their definitions below.

PE (transesterified egg phosphatidylethanolamine)
PC (phosphatidylcholine)
DPPC (dipalmitoylphosphatidylcholine)
DTNB (5,5-dithiobis 2-nitrobenzoic acid)
CDI (carbonyldeimidazole)
DDT (dithiothreitol)
SPDP (N-succinimidyl 3-(2-pyridyldithio)propionate)
2-TP (2-Thiopyridinone)
PDP-PE (N-[3-(2-Pyridyldithiopropionyl] phosphatidylethanolamine)
SMPB (succinimidyl 4-(p-maleiminidophenyl) butyrate)
MPB-PE (N-[4-(p-maleimidophenyl) butyryl] phosphatidyethanolamine)
SUV (small unilamellar vesicles)
LUV (large unilamellar vesicles)
REV (reverse phase evaporation)
Buffer I (100 mM NaCl, 100 mM borate, 50 mM citrate, and 2 mM EDTA)
Buffer II (35 mM NaCl, 100 mM borate, 50 mM citrate, and 2 mM EDTA)
Buffer IA (35 phosphate, 20 mM citrate, 108 mM NaCl and 1 mM EDTA)

EXAMPLE I

PDP-PE LIPOSOMES

Synthesis of PDP-PE.

PE (50 μmol) was dissolved in 3 mL of anhydrous methanol containing 50 μmol of triethylamine and 25 mg of SPDP. The reaction was carried out at 25° C. under an argon atmosphere. Following 5 h, TLC of the reaction mixture revealed quantitative conversion of the PE to a faster running product. Methanol was removed under reduced pressure, and the products were redissolved in chloroform and applied to a 10-mL silica gel column which had been activated (150° C. overnight) and prewashed with 100 mL of chloroform. The column was washed with an additional 20 mL of chloroform followed by 20 mL of each of the following chloroform-methanol mixtures 40:1, 30:1, 25:1, 20:1, and 15:1 and, finally, with 60 mL of 10:1 chloroform-methanol. The phosphate-containing fractions eluting in 15:1 and 10:1 chloroform-methanol were pooled and concentrated under reduced pressure.

Analysis by TLC (silica gel H; solvent chloroform-methanol-acetic acid, 60:20:3) indicated a single phosphate-positive, ninhydrin- and sulfhydryl-negative spot. Identification of the product as the (pyridyldithio)propionyl derivative of PE was confirmed by our observation that a stoichiometric amount of 2-thiopyridinone (2-TP) is released upon the addition of excess DTT. No detectable decomposition of PDP-PE was observed for periods of up to 6 months when stored in glass ampules under argon at −50° C.

Figure I, below, generally illustrates the above described reaction scheme.

FIG. I

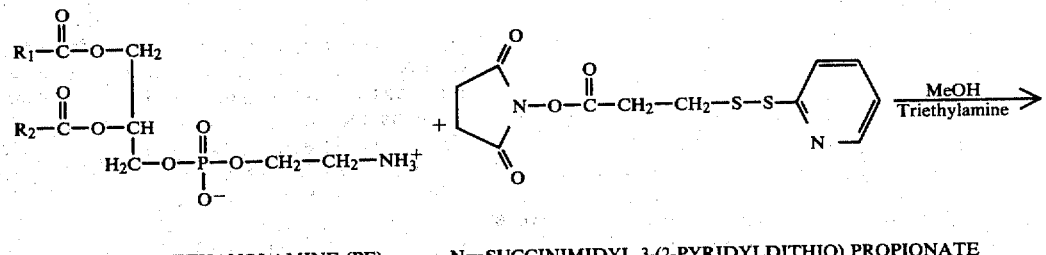

PHOSPHATIDYLETHANOLAMINE (PE)    N—SUCCINIMIDYL 3-(2-PYRIDYLDITHIO) PROPIONATE (SPDP)

-continued
FIG. I

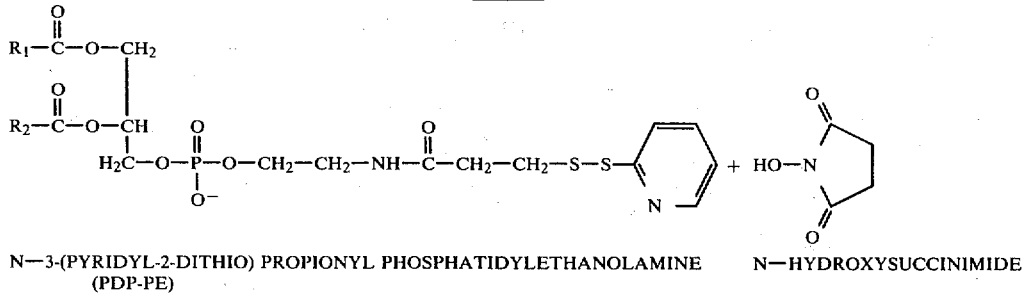

N—3-(PYRIDYL-2-DITHIO) PROPIONYL PHOSPHATIDYLETHANOLAMINE (PDP-PE)  N—HYDROXYSUCCINIMIDE (where $R_1$ and $R_2$ are traditionally carbon chains of various lengths)

Preparation of Vesicles.

Vesicles were prepared by the reverse-phase evaporation method of Szoka & Papahadjopoulos (1978) *Proc. Natl. Acad. Sci. U.S.A.*, Volume 75, No. 9, pp. 4194–4198, also disclosed by U.S. Pat. No. 4,235,871. Briefly, 10 μmol of cholesterol, 9 μmol of PC, 1 μmol of PDP-PE and a trace amount of [$^3$H]DPPC were dissolved in 1 mL of freshly distilled diethyl ether. Buffer I (pH 6.0) (0.3 mL) was added, and the two phases were emulsified by sonication for 2 min at 25° C. in a bath-type sonicator. Ether was removed under reduced pressure at 30° C. The resulting vehicle dispersion was extruded through 0.4- and 0.2- μm pore Bio-Rad Laboratories Uni-Pore polycarbonate membranes, as is described in U.S. Pat. No. 4,263,428, issued Apr. 21, 1981, to produce uniformly sized vehicles. For determination of internal volumes, vesicles were prepared in the presence of 0.3 M sucrose and a trace amount of [$^{14}$C] sucrose. The internal volume was calculated from the amount of sucrose (specific activity of [$^{14}$C] sucrose) remaining after removal of unentrapped solute by gel filtration on Sephadex G-25. Sucrose efflux, expressed as the proportion of sucrose remaining entrapped for periods up to 24 h, was determined by dialysis.

Characterization of Vesicles.

Electron microscopic observations reveal that vesicles composed of PC, cholesterol, and PDP-PE (45:50:5), prepared by the reverse-phase evaporation method and extruded through 0.2- μm pore membranes, are spherical in shape and range in diameter from about 500 Å to 0.5 μm. The vast majority of vesicles, however, fall in the size range of 1000–3000 Å, the mean diameter being about 1900 Å. Occasional multilamellar vesicles are visible in such EM preparations.

The encapsulated volume of such vesicles, calculated from the specific activity of [$^{14}$C] sucrose remaining associated with vesicles following removal of the unentrapped solute by gel filtration, is 4.5±0.3 μL/μmol of vesicle phospholipid, slightly less than the predicted value of 6.4 μL/mol, assuming that all vesicles are single layered and 0.2 μm in diameter. The permeability of these vesicles to sucrose was found to be quite low. The rate of sucrose efflux is less than 1%/h at 25° C.

The low value for sucrose encapsulation together with the EM results suggests that a small proportion of the PC-cholesterol-PDP-PE vesicles used in this study are multilamellar. In order to determine more precisely the average number of lamellae per vesicle, we have synthesized a reducing agent, DHLA-dextran T-20, which cannot permeate vesicle bilayers but is capable of reducing the pyridyl disulfide moiety of PDP-PE molecules that are exposed in the outer monolayer of vesicles. We have measured the appearance of 2-TP, which is released as a product of PDP-PE reduction, to determine the proportion of PDP-PE molecules present in preformed vesicles that are accessible to this impermeable reducing agent. 54.5 nmol of 2-TP is released within 5 min following the addition of excess DTT (which freely permeates vesicle bilayers) to a suspension of PDP-PE-containing vesicles (0.5 μmol of total phospholipid). This corresponds closely to the expected value of 50 nmol (0.1 mol fraction of the total phospholipid in these vesicles is PDP-PE).

Figure II, below, illustrates a thiol reactive liposome of the PDP-PE species, with the PDP-PE lipid component being enlarged relative the diagrammatic representation of the lipid bilayer which forms the liposomal outer surface.

FIG. II

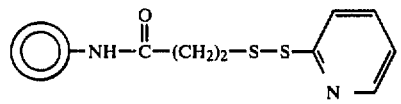

PDP-PE Vesicle

As may be understood, the particular —($CH_2$)$_2$— organic spacer arm of the Figure II structure, above, may vary (for example—($CH_2$)$_n$— where n is the integer 1 or greater).

EXAMPLE II

MPB-PE LIPOSOMES

Synthesis of MPB-PE:

Transesterified egg PE (100 μmol) was dissolved in 5 ml anhydrous methanol containing 100 μmol freshly distilled triethylamine and 50 mg succinimidyl 4-(p-maleimindo phenyl) butyrate (SMPB). The reaction was carried out under an argon atmosphere at room temperature. Thin layer chromatography of the mixture following two hours revealed quantitative conversion of the PE to a faster running product ($R_f$ 0.52, silica gel H, solvent: chloroform-methanol water, 65:25:4). Methanol was removed under reduced pressure and the products redissolved in chloroform. The chloroform phase was extracted twice with 1% NaCl to remove unreacted SMPB and water soluble byproducts. The MPB-PE was further purified by silicic acid chromatography as described for PDP-PE. Following purification, TLC indicated a single phosphate positive, ninhydrin-negative spot. MPB-PE is stable for at least 4 months when stored at −50° C. as a chloroform solution sealed in glass ampules under argon. Figure III, below, generally illustrates the above described reaction scheme.

FIG. III

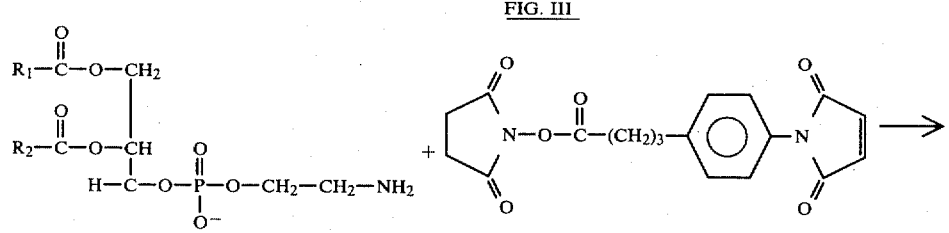

PHOSPHATIDYLETHANOLAMINE    N—SUCCINIMIDYL 4-(P—MALEIMIDOPHENYL) BUTYRATE

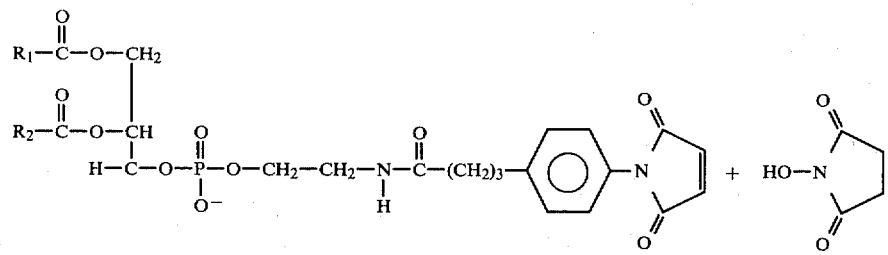

N—4-(P—MALEIMIDOPHENYL) BUTYRYL PHOSPHATIDYLETHANOLAMINE   N—HYDROXYSUCCINIMIDE

Preparation of Vesicles:

LUV were prepared by the reverse phase evaporation method of Szoka and Papahadjopoulos, supra, with minor modifications. Briefly, 10 μmol cholesterol, 0.5 μmol PC, 0.5 μmol MPB-PE and a trace amount of ($^3$H)DPPC were dissolved in 1 ml diethyl ether. Buffer (20 mM citric acid, 35 mM disodium phosphate, 108 mM NaCl, 1 mM EDTA, pH 4.5) was added (300 μl) and the two phases emulsified by sonication for 1 min at 25° C. in a bath-type apparatus. Ether was removed under reduced pressure at room temperature and the resulting vesicle dispersion extruded through 0.4μ and 0.2μ Uni-Pore polycarbonate membranes (Bio-Rad Laboratories).

The size, encapsulated volume and substantially unilamellar characteristics of the MPB-PE vesicles were substantially as described for PDP-PE vesicles, above.

Figure IV, below, illustrates a thiol reactive liposome of the MPB-PE species, with the MPB-PE lipid component being enlarged relative the diagrammatic representation of the lipid bilayer forming the liposomal outer surface.

FIG. IV

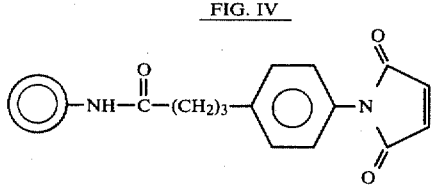

MPB-PE Vesicle

As may be understood, the particular —(CH$_2$)$_3$—φ— organic spacer arm of the Figure IV structure, above, may vary. For example, where —(CH$_2$)$_n$— and n is 1 to about 6, and where the maleimide moiety is substituted at a meta or ortho position on the phenyl group.

EXAMPLE III
S-SULFONATE LIPOSOMES

S-sulfonate liposomes are prepared in a manner analogous to Examples I and II, with the reaction scheme for sulfonation of PE being in accordance with the method of Oeltmann and Heath, *J. Biol. Chem.* 254: 1022–1027 (1979) and generally represented by Figure V, below, and the particular S-sulfonate species of the thiol reactive liposomes being illustrated by Figure VI in a similar manner to that of Figures II and IV.

FIG. V

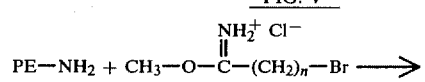

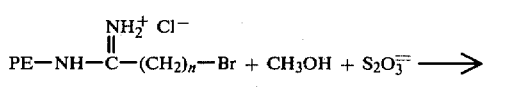

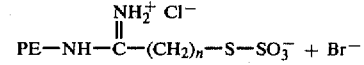

FIG. VI

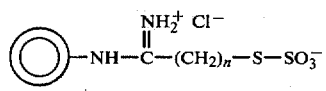

As may be understood, the —(CH$_2$)$_n$— organic spacer arm of Figure VI, above, may vary (and originates from n of Figure V), normally wherein n is an integer from 1 to about 6.

EXAMPLE IV
HALOACETYL LIPOSOMES

Haloacetyl liposomes are prepared in a manner analogous to Examples I and II, with the reaction scheme for sulfonation of PE being in accordance with the method of Rector, et al., *J. Immuno. Methods* 24: 321–336 (1978) and generally represented by Figure VII, below, and the particular haloacetyl species of the thiol reactive liposomes being illustrated by Figure VIII in a similar manner to that of Figures II and IV.

FIG. VII

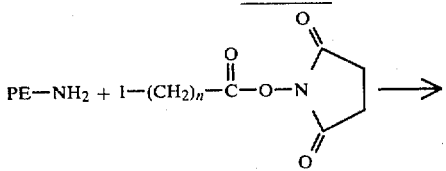

FIG. VIII

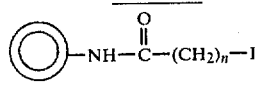

wherein n is normally 1 to about 6.

Coupling of Ligands to the Thiol Reactive Liposomes

The thiol reactive liposomes are adapted to react with ligands having reactive thiol groups. As used herein, ligand means a compound which can interact specifically but non-covalently with a ligand-binding molecule, or receptor. One type of such interaction is antigen-antibody, another is hormone-receptor, and yet another is carbohydrate-lectin.

Particularly preferred ligands for coupling to the thiol reactive liposomes are Fab' antibody fragments, each of which contains a single reactive thiol group at a defined position on the molecule. As is well known, the IgG immunoglobulin molecule has a molecular weight of about 150,000 d and possesses four peptide chains linked together by disulfide bonds. Upon enzymatic digestion with pepsin, the Fc portions of the heavy chains are cleaved. Treatment of the F(ab')2 antibody fragments with DTT under suitable conditions results in the selective reduction of the interheavy-chain disulfide bond of this molecule and thereby produces two monomeric Fab' fragments. Each monomer produced by this method contains about one sulfhydryl group which is at one end of the monomer, while the antigen binding site is distal therefrom. Use of Fab' fragments for coupling to the inventive liposomes is also preferred for many applications, as the absence of a Fc region eliminates the possibilities of Fc-mediated binding and complement activation, and reduces the likelihood of anti-idiotypic antibody production in vivo.

Where the ligands to be coupled to the thiol reactive liposomes of the present invention do not contain a reactive thiol group, then such ligands will be thiolated.

The thiol reactive liposomes form covalent bonds with suitable ligands. These covalent bonds may be generally characterized as disulfide bonds or thio ether bonds. Thus, for example, the PDP-PE and S-sulfonate liposomes couple with Fab' fragments by means of disulfide linkages, whereas the MPB-PE and haloacetyl liposomes couple by means of a thioether linkage.

As will be more fully discussed hereinafter, the MPB-PE liposomes are most preferred for coupling with thiol reactive ligands, particularly Fab' fragments, due to the substantially irreversible coupling of immunoglobulin fragments to the MPB-PE vesicles. Thus, extremely stable couplings result. For example, serum does not cause elution of conjugated Fab' from the MPB-PE vesicles nor does it interfere with binding of liposomes to cells. This is believed to be particularly important, as many clinical applications of coupled liposome-ligand conjugates will require exposure to serum for considerable periods of time.

Examples V and VI, below, illustrate preparation of Fab' antibody fragments and coupling thereof to PDP-PE vesicles and MPB-PE vesicles respectively.

EXAMPLE V

Preparation of Fab' Antibody Fragments.

The coupling method for the covalent attachment of antibody fragments to the surfaces of lipid vesicles depends on the availability of thiol groups on the antibody fragments capable of participating in a disulfide interchange reaction with the (pyridyldithio)propionyl moiety of PDP-PE molecules present in the outer monolayer of preformed vesicles. For minimization of vesicle aggregation due to cross-bridging, a single thiol group per antibody fragment is desirable. Conditions for the preparation of 50,000-dalton Fab' antibody fragments, each of which contains a single reactive thiol group at a defined position on the molecule, were as follows.

Treatment of rabbit F(ab')2 antibody fragments with DTT (20 mM) at low pH (5.5) for 90 min at 25° C. results in the selective reduction of the inter-heavy-chain disulfide bond of this molecule and thereby produces two monomeric Fab' fragments. Titration of Fab' fragments with Ellman's reagent reveals that each monomer produced by this method contains, on the average, 0.95 sulfyhdryl group. Gel filtration on Sephadex G-75 indicates that greater than 95% of the F(ab')2 fragments is converted to the 50K Fab' during such a reduction. Moreover, when antihuman erythrocyte F(ab')2 fragments are subjected to similar DTT treatment, the capacity of the fragments to agglutinate human erythrocytes is reduced 64-fold (the HA titer of a 10 gm/mL solution falls from 8192 to 128).

Upon the removal of DTT, Fab' monomers are unstable and tend to re-form F(ab')2 dimers as the result of an oxidative reaction between the sulfyhydryl groups exposed on each Fab' fragment. The rate of F(ab')2 formation (measured as the reduction in the number of titratable thiol groups) is dependent on the pH and the availability of molecular oxygen. Two hours after the removal of DTT, in the absence of $O_2$, the number of thiol groups per Fab' monomer is reduced to 0.75 at pH 6.0 and to 0.50 at pH 8.0. In the presence of molecular oxygen, the rate of F(ab')2 formtion is accelerated, and essentially complete reannealing is observed within 2 h at pH 8.0.

Despite the tendency of Fab' molecules to recombine into the dimer form at alkaline pH, this competing reaction does not appear to be rate limiting with respect to vesicle coupling. The addition of freshly reduced Fab' fragments at 30-min intervals during the course of a coupling reaction does not significantly improve coupling ratios. The preparation as above described is illustrated by Figure IXA, below.

Coupling of Fab' Fragments to PDP-PE-Containing Vesicles.

The protocol we have followed in order to obtain covalent coupling of Fab' antibody fragments to PDP-PE-containing vesicles is illustrated by Figure IXB, below. PDP-PE vesicles are mixed with Fab' fragments (about 3 μmol of phospholipid and 1–12.5 mg of Fab') immediately following the removal of DTT (see preceding section). The pH is adjusted to 8.0 and the coupling reaction allowed to proceed for 2 h under argon. Unreacted antibody fragments are then removed by gel filtration.

A mixture of control vesicles (PC-cholesterol, 50:50) and nonspecific rabbit Fab' fragments was chromatographed on Sephadex G-150. From the elution profile, the vesicles appear in the void volume of such a column while the antibody fragments elute with the included volume. No binding of Fab' fragments to control vesicles is evident. However, when 5 mol % of PDP-PE is included in the vesicle membrane, a significant proportion (approximately 30%) of the added Fab' coelutes with the vesicles. When fractions from this coeluant are pooled, concentrated, and rechromatographed on Sephadex G-150, all of the Fab' coelutes with the vesicle peak, indicating a stable association between Fab' molecules and vesicles. This Fab'-vesicle binding is completely reversible, however, in the presence of 50 mM DTT at pH 8.0. These results suggest that Fab' binding results from the formation of reversible disulfide cross-linkages between Fab' fragments and vesicles.

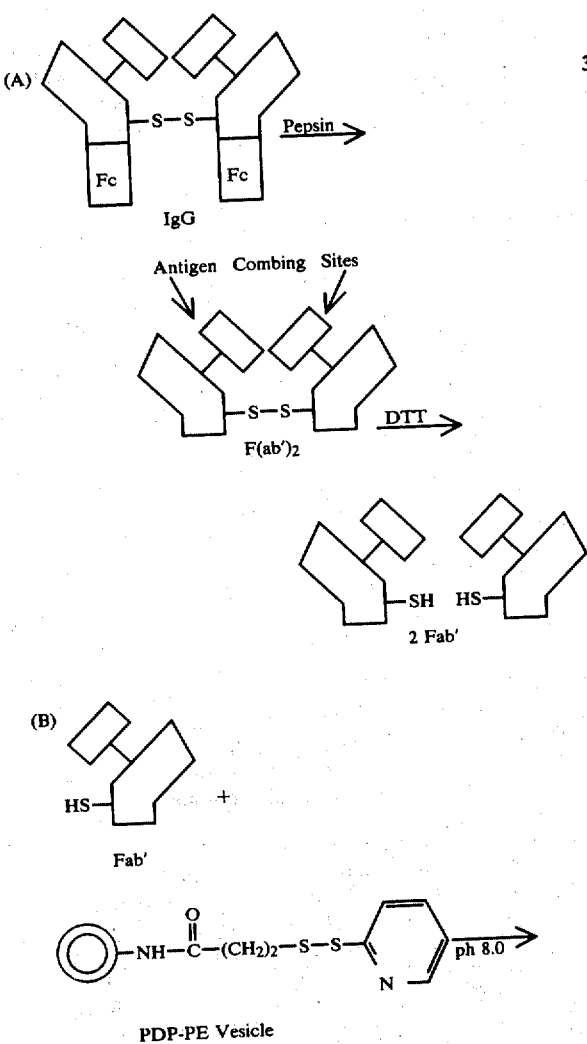

FIG. IX

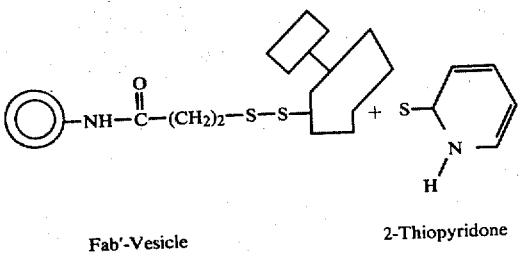

Fab'-Vesicle        2-Thiopyridone

-continued
FIG. IX

EXAMPLE VI

Preparation of Antibody Fragments:

Fab' fragments of nonspecific rabbit IgG and anti hRBC-F(ab')$_2$ fragments were prepared and purified as described in Example V, above, except Buffer IA(pH 5.0) containing 20 mM dithiothreitol was used for the reduction step. F(ab')$_2$ fragments were radiolabeled with $^{125}$I to a specific activity of ~2×10$^6$ cpm/mg prior to reduction.

Coupling of Fab' Fragments to MPB-PE Vesicles:

The protocol of covalently coupling Fab' antibody fragments to MPB-PE vesicles is illustrated by Figure X, below. Vesicles (PC-Cholesterol-MPB-PE; 9.5:10:0.5) prepared by the reverse-phase evaporation method and extruded through 0.2 μUni-Pore membranes, entrapped about 15% of the original aqueous volume (4.73 μl/μmol phospholipid). Sucrose efflux was less than 0.5% per hour in Buffer I at 25° C. and less than 3% per hour in 50% serum. The half-life of the maleimide was greater than 4 hours in Buffer I at pH 4.5–6.5.

Fab' fragments prepared as described above contained an average of 0.85-SH groups per molecule. The half-life of the —SH was 4–5 hours in Buffer IA (pH 6.5).

MPB-PE containing vesicles (1.4 μmol/ml) were reacted with freshly reduced Fab' fragments (0.5–0.4 mg/ml) for 8 hours at 25° C. When such mixtures were chromatographed on Sephadex G-200, 20–30% of the Fab' coeluted with vesicles in the void volume. The Fab' remained with vesicles during rechromatography, indicating a stable association. When exposed to a 1:32 dilution of goat anti-rabbit IgG serum, greater than 95% of both the ($^{125}$I)Fab' and ($^3$H)DPPC labels coprecipitated suggesting a rather homogeneous lipid to protein ratio. Nonspecific binding of Fab' to control vesicles (PC-cholesterol, 1:1) was less than 4 μg/μmol phospholipid at Fab' concentrations below 5 mg/ml.

FIG. X

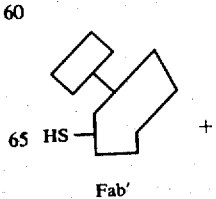

Fab'

-continued
FIG. X

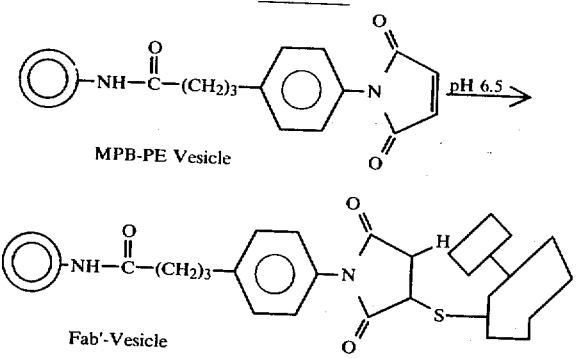

MPB-PE Vesicle

Fab'-Vesicle

We found a linear relationship between the amount of Fab' bound to vesicles (in 8 hours) and the initial Fab' concentration. For antibody concentrations of 0.5, 2.0 and 4.0 mg/ml, we obtained coupling ratios of 70±15, 330±20 and 584±40 μg Fab' per μmol vesicle phospholipid, respectively. Some aggregation of vesicles occurred at Fab' concentrations above 4 mg/ml.

In a typical coupling reaction, approximately 340 μg of the Fab' was coupled to vesicles in 8 hours. This value corresponds to greater than 3000 Fab' molecules per each vesicle (0.2μ diameter). The time course of Fab' coupling to PDP-PE vesicles at pH 8.0 and equivalent protein and lipid concentrations, by comparison, was less efficient than the reaction of Fab' with maleimide-PE at pH 6.5.

Thiol reactive liposomes in accordance with the present invention form quite stable covalent bonds with Fab' fragments. For example, about 92% of the original Fab' remains associated with PDP-PE vesicles during an 8 hour incubation at pH 8.0 in DTT, and about 62% of the original Fab' remains associated in 50% human serum. The most preferred embodiment of MPB-PE vesicles, when coupled with Fab', results in no coupled Fab' being lost from the MPB-PE vesicles during incubation for 24 hours in DTT (50 mM, pH 7.5) or human serum (50%, pH 7.4). Table I, below, illustrates stability data for Fab' coupled with PDP-PE vesicles and MPB-PE vesicles, respectively.

TABLE I (a) Fab' fragments covalently coupled to PDP-PE vesicles:

| | μg of Fab'/μmol of phospholipid | | Fab' remaining coupled after 8 h (%) |
|---|---|---|---|
| | start | 8 h, 25° C. | |
| pH 6.0 | 286 | 277 | 97 |
| pH 7.0 | 286 | 272 | 95 |
| pH 8.0 | 286 | 263 | 92 |
| 25% human serum | 286 | 212 | 74 |
| 50% human serum | 286 | 177 | 62 |

(b) Fab' fragments covalently coupled to MPB-PE vesicles:

| | μg of Fab'/μmol of phospholipid | | Fab' remaining coupled after 24 h (%) |
|---|---|---|---|
| | start | 24 h, 25° C. | |
| pH 7.5* | 340 | 326 | 96 |
| 50% human serum | 340 | 319 | 94 |

*50 mM DTT

As has previously been noted, where the ligand to be coupled does not have reactive thiol groups, then it will be thiolated prior to coupling with the thiol reactive liposomes. Proteins, and particularly antibodies, are desirably thiolated (assuming fragments such as Fab', which already bear sulfhydryl groups, are not being used) for various immunodiagnostic applications. This is illustrated by Example VII, below.

EXAMPLE VII

MPB-PE was synthesized as has already been described. Liposomes were then prepared by the method of Szoka and Papahadjopoulos, supra, from 10:10:1 phosphatidylcholine:cholesterol:MPB-PE in a buffer at pH 6.0–6.7. A suitable buffer is 0.05 M morpholinoethanesulfonic acid, 0.096 M NaCl, pH 6.4. It is preferred to prepare the vesicle below pH 7.0 to ensure the maximal stability of the maleimide function.

Six antibody preparations were pyridylthiolated and reduced by the method of Carlsson et al. Biochem. J., 173, pp. 723–737 (1978). Reaction of protein with 10 mole of SPDP per mole of protein results in the substitution of 3–5 mole of pyridyldithiol groups per mole protein. After reduction with dithiothreitol, the protein was separated from the reducing agent on a polyacrylamide column (50 to 100 mesh) equilibrated in argon-purged (de-oxygenated) buffer, pH 6.0–6.5. The protein fractions were pooled and concentrated to a suitable volume under argon in an amicon type concentrator. Commonly, the protein is concentrated to around 3 mg/μl. MPB-PE liposomes were then added to the protein solution with stirring to give 5 μmole lipid per ml. After reaction overnight, the vesicles are reacted with Aldrithiol 4 and separated on a metrizamide gradient and the protein and lipid are determined.

The protein, or antibody, was modified by from about 1.8 to about 5.1 thiols per molecule.

The six coupled liposome-antibody compositions were as illustrated by Table II, below.

TABLE II

| coupled antibody | antibody to lipid ratio (μg/μmole) |
|---|---|
| Normal human IgG | 235 |
| anti H2K$^k$ (2)* | 52 |
| Mouse IgG (A11)* | 128 |
| anti glycophorin (1)* | 240 |
| anti sheep RBC (2a)* | 2000 |

*wherein the symbol within the parentheses gives the IgG subclass of the antibody The present invention is particularly useful for coupling the thiol reactive liposomes to sufficient of a biologically active antibody and then using the coupled liposome-antibody compositions in agglutination assays such as blood typing and binding inhibitions.

Many prior attempts to covalently attach protein to lipsomes had been unsatisfactory. For example, some of the prior attempts had involved modifications of the proteins which tended to denature the protein, and thus a substantial loss of biological activity had ensued. Other attempts to covalently attach protein to liposomes had produced very small amounts of specific attachment.

However, liposomes which could be readily and efficiently covalently bound to a variety of biologically active proteins, with at least about 40 microgram of protein per micromole of lipid up to about 200 μg/μmol, have been produced via glycosphingolipids, as reported by Heath et al., in Science, Vol. 210, pp. 539–541 (1980) in Biochimica et Biophysica Acta, 640, pp. 66–81 (1981), and as described by U.S. patent application Ser. No. 129,654, filed Mar. 12, 1980 of common assignment herewith. The liposomes of Heath et al, when coupled with antibody, were found to have an improved capacity to agglutinate erythrocytes with respect to the original, soluble antibody from which the liposome-protein conjugates were derived. This improved capacity, and the use of covalently bound liposome-protein conjugates as reagents in agglutination methods, particularly for hemagglutination assays, is described in a continuation-in-part application of Ser. No. 129,654 (e.g. Ser. No. 316,126, filed Oct. 29, 1981, also of common assignment herewith).

The thiol reactive liposomes of the present invention, when coupled to antibody, likewise display a capacity to agglutinate erythrocytes which is improved with respect to the original, soluble antibody. For example, liposomes were formed from PC:cholesterol:PDP-PE and conjugated to Fab' as has been previously described. The coupled liposome-protein conjugates had 50 µg of antihuman erythrocyte Fab' fragments per µmole liposomal phospholipid (about 500 antihuman Fab' fragments per liposome). The minimum hemagglutinating concentration (MHC) for soluble antibody was 5.2 µg/ml, whereas the MHC for liposome-protein conjugates was 0.17 µg/ml. That is, the agglutination improvement factor was about 30.

Liposomes formed from PC:cholesterol:MPB-PE (9.5:10:0.5) and conjugated to Fab' (anti hRBC), as previously described, had 340 µg of antihuman erythrocyte Fab' fragments per µmole of liposomal phospholipid. The minimum hemagglutination concentration (MHC) for soluble antibody was 4.6 µg/ml, whereas the MHC for these liposome-protein conjugates was 0.073 µg/ml. That is, the agglutination improvement factor was about 60.

It is believed that the characteristics of these covalently bound liposome-protein conjugates which contribute to enhanced agglutination capacity include multivalency (as each vesicle may contain up to several thousand antigen binding sites), and the size of the vesicles (preferably from about 0.02 micron to about 5 micron, more preferably about 0.1 to about 0.5 micron) relative to cells is believed to favor cell bridging and lattice formation. Also, the thio reactive groups protrude from the outer liposomal surface by flexible chemical "spacer arms" so that when antibody molecules are coupled, they are orientated as to favor binding to buried or "crytic" antigens on cell surfaces.

The excellent stability in serum of MPB-PE vesicles is believed to be particularly advantageous for cytoplasmic delivery of liposomal contents with, for example, monoclonal antibodies as the coupled ligand and actively metabolizing cells as targets.

We claim:

1. A composition, useful for conjugation with ligands bearing thiol groups, comprising:
    liposomes, each liposome having a lipid bilayer defining an outer surface for the liposome, and a plurality of thiol reactive groups integrally connected to the lipid bilayer and extending outward with respect to the outer surface.

2. The composition as in claim 1 wherein:
    the thiol reactive groups are at polar head regions of nitrogen containing lipids, the thiol reactive groups being bound to the nitrogen containing lipids by amide or amidine linkages, the nitrogen containing lipids being components of the lipid bilayer.

3. The composition as in claim 1 or 2 wherein:
    the thiol reactive groups of the liposomes are adapted to form disulfide or thio ether bonds with ligands.

4. The composition as in claim 1 or 2 wherein:
    the thiol reactive groups of the liposomes are adapted to form stable thio ether bonds with IgG fragments bearing sulfhydryl groups.

5. The composition as in claim 2 wherein:
    the polar head regions of the nitrogen containing lipids include maleimide moieties spaced from the amide or amidine linkages of the nitrogen containing lipids by organic spacer arms.

6. The composition as in claim 1 or 2 wherein:
    the thiol reactive groups are adapted to form disulfide bonds with biologically active IgG fragments bearing sulfhydryl groups.

7. The composition as in claim 6 wherein:
    the thiol reactive groups are

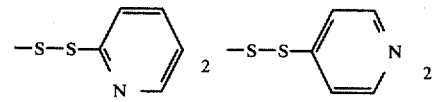

or —S—SO₃, and are spaced from the amide or amidine linkages of the nitrogen containing lipids by organic spacer arms.

8. A composition, useful for coupling with proteins, comprising:
    liposomes including lipid molecules, each liposome having a lipid bilayer defining an outer surface for the liposome, at least some of the lipid molecules having amide or amidine linkages in the polar head regions by which moieties having the structure

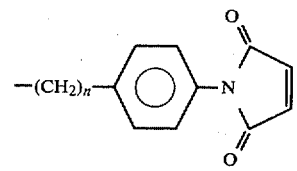

where n is about 1 to about 6, are bound, the bound moieties being positioned outward with respect to the liposomal outer surfaces.

9. The composition as in claim 8 wherein:
    the liposomes are substantially discrete, unilamellar vesicles.

10. The composition as in claim 9 wherein:
    the liposomes have a diameter of from about 0.02 micron to about 5 micron.

* * * * *

UNITED STATES PATENT AND TRADEMARK OFFICE
CERTIFICATE OF CORRECTION

PATENT NO. : 4,429,008

DATED : Jan. 31, 1984

INVENTOR(S) : Martin et al.

It is certified that error appears in the above-identified patent and that said Letters Patent is hereby corrected as shown below:

Column 18, line 30: the "2" appearing after both chemical structures should read --,--.

Signed and Sealed this

Twenty-fourth Day of April 1984

[SEAL]

Attest:

GERALD J. MOSSINGHOFF

Attesting Officer    Commissioner of Patents and Trademarks

REEXAMINATION CERTIFICATE (2576th)

United States Patent [19]

Martin et al.

[11] B1 4,429,008

[45] Certificate Issued   May 16, 1995

[54] THIOL REACTIVE LIPOSOMES

[75] Inventors: Frank J. Martin, San Francisco; Demetrios P. Papahadjopoulos, Lafayette; Wayne L. Hubbell, Orinda, all of Calif.

[73] Assignee: The Regents of the University of California, Berkeley, Calif.

Reexamination Request:
No. 90/003,545, Aug. 24, 1994

Reexamination Certificate for:
Patent No.: 4,429,008
Issued: Jan. 31, 1984
Appl. No.: 329,211
Filed: Dec. 10, 1981

Certificate of Correction issued Apr. 24, 1984.

[51] Int. Cl.$^6$ .................... A61K 9/127; A61K 9/133; B01J 13/02; B32B 9/02
[52] U.S. Cl. ................................ 428/402.2; 424/1.21; 424/178.1; 424/194.1; 436/501; 436/532; 436/829
[58] Field of Search ................... 428/402.2; 436/501, 436/829; 424/1.21, 450

[56] References Cited

U.S. PATENT DOCUMENTS

| | | | |
|---|---|---|---|
| 3,516,941 | 6/1970 | Matson | 264/4.7 X |
| 3,850,578 | 11/1974 | McConnell | 436/536 |
| 3,887,698 | 6/1975 | McConnell et al. | 424/12 |
| 4,193,983 | 5/1978 | Ullman et al. | 424/12 |
| 4,199,565 | 4/1980 | Fullerton | 424/89 |
| 4,235,792 | 11/1980 | Hsia et al. | 436/829 X |
| 4,342,739 | 8/1982 | Kakimi et al. | 424/402.2 X |

OTHER PUBLICATIONS

Martin, F., "Immunospecific targeting of Liposomes to Cells: A Novel and Efficient Method . . . Disulfide Bonds", *Biochemistry* 20, (Jul. 1981) 4229–4238.

Torchilin, V. P., et al. "Incorporation of Hydrophilic Protein . . . into Lipsosome Membrane", *Biochimica et Biophysica Act*, 602 (1980) 511–521.

Torchilin, V. P., et al. "Preservation of Antimyosin . . . to Liposomes", *Biochemical and Biophysical Reserach Communications*, 89, #4, (1979) 1114–1119.

Huang, A. et al. "Monoclonal Antibody Covalently and coupled with Fatty Acid", *Journal of Biological Chemistry* 255, #17 (1980) 8015–8018.

Torchilin, V. P., et al "Coating Liposomes with Protein Decreases their Capture by Macrophages", *FEBS Letters*, 111, #1, (1980) 184–188.

Leserman, L. et al., "Targeting to Cell of Fluorescent Liposomes . . . or Protein A", *Nature* 28 (Dec. 11, 1980) 602–604.

Heath, T. et al., "Antibody Targeting of Liposomes: Cell . . . to Vesicle Surface," *Science* 210 (Oct. 31, 1980) 539–541).

Heath, T. et al., "Covalent Attachment of Immunoglobulins to Liposomes via Glycosphingolipids," *Biochimica et Biophysica Acta*, 640 (1981) 66–81.

Torchilin, V. P. et al., "Comparative Studies on Covalent . . . on the Surface of Liposomes", *BBRC*, vol. 85, No. 3, pp. 983–990 (1978).

Sinha, D. et al., "Conjugation of a Hydrophobic Anchor . . . to Liposomal Membranes", FEBS Proc. Abstracts (May 1, 1980).

Sinha, D. et al., "Attachment to Membranes of Exogenous . . . to a Hydrophobic Anchor" *BBRC*, vol. 90, No. 2 (1979), 554–560.

Carlsson, J. et al., "Protein Thiolation and Reversible Protein-Protein Conjugation" *Biochem. J.*, 173, (1978) 723–737.

Oeltmann, et al., "A Hybird Protein Containing the Toxic . . . of Human Chorionic Gonadotropin" *J. Bio. Chem.*, vol. 254, No. 4 (1979), 1022–1027.

Rector, et al., "A Method for the Preparation . . . of Predetermined Composition", *J. Immuno. Methods*, 24, (1978) 321–326.

Leserman, L. D., et al., "Cell-Specific Drug Transfer from Liposomes Bearing Monoclonal Antibodies" *Nature*, vol. 293, pp. 226 (1981).

Barbet, et al., "Monoclonal Antibody Covalently Coupled to Lipsomes", *J. Supramolec. Structure and Cellular Biochem.*, vol. 16, pp. 243–258 (1981).

Uemura, Kei-ichi et al, "Active vs., Passive Sensitization of Liposomes toward Antibody and Complement by Dinitrophenylated Derivatives of Phosphatidylethanolamine" *Biochemistry* vol. 11. No. 20 (1972) 4085–4094.

King, Te Piao et al., "Preparation of Protein Conjugates via Intermolecular Disulfide Bond Formation" *Biochemistry* vol. 17, No. 8 (1978) 1499–1506.

Heath, T. et al., "Covalent Attachment of Horseradish Peroxidase to the Outer Surface of Liposomes" *Biochimica et Biophysica Acta*, 599 (1980) 42–62.

Dunnick et al. "Vesicle Interactions with Polyamino Acids and Antibody": In Vitro and In Vivo Studies *Journal of Nuclear Medicine* vol. 16, No. 6 pp. 483–487.

Leserman, et al., "Liposomes Directed to Specific Cellular Targets by Covalently-Coupled Monoclonal Antibody, Protein A, and Avidin", Satellite Symposium of the IV International Congress of Immunology, Paris, *Antibodies As Carriers of Anticancer Drugs of Toxins: Quo Vadis? (Jul. 17, 1980).*

*Primary Examiner*—Richard D. Lovering

[57] ABSTRACT

Liposomes are provided which have a plurality of thiol reactive groups extending outward of the liposomal bilayer. The liposomes form stable covalent bonds with ligands having thiol groups, such as $Fab^1$ fragments. Particularly preferred liposomes include maleimide moieties as the thiol reactive groups. The thiol reactive liposomes are usefully employed in agglutination assays, such as blood typing and binding inhibitions, and targeting to specific cells.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 8–10 is confirmed.

Claims 1, 3, 6 and 7 are determined to be patentable as amended.

Claims 2, 4 and 5, dependent on an amended claim, are determined to be patentable.

1. A composition, useful for conjugation with ligands bearing thiol groups, comprising:
   liposomes, each liposome having a lipid bilayer defining an outer surface for the liposome, and a plurality of thiol reactive groups integrally connected to the lipid bilayer and extending outward with respect to the outer surface, wherein the thiol reactive groups are adapted to form thio ether bonds with ligands.

3. The composition as in claim 1 or 2 wherein:
   the thiol reactive groups of the liposomes are [adapted to form disulfide or thio ether bonds with ligands] *maleimide moieties*.

6. The composition as in claim [1 or 2] *5* wherein:
   [the thiol reactive groups are adapted to form disulfide bonds with biologically active IgG fragments bearing sulfhydryl groups] *the organic spacer arms have the formula*

$$-(CH_2)n-,$$

*where n is an integer greater than 1.*

7. The composition as in claim 6 wherein:
   [the thiol reactive groups are

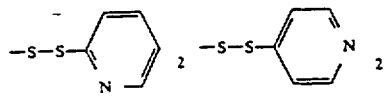

or -S-SO$_3$, and are apaced from the amide or amidine linkages of the nitrogen containing lipids by organic spacer arms] *n is an integer from 1 to about 6.*

* * * * *